United States Patent [19]

Delavarenne et al.

[11] 4,297,288

[45] Oct. 27, 1981

[54] 5-AMINO-1,2,3,4-TETRAHYDROAN-THRAQUINONE AND ITS PREPARATION

[75] Inventors: Serge Y. Delavarenne, Francheville Le Haut; Bernard Dubreux, Francheville Le Bas; Pierre Tellier, Sainte Foy Les Lyon, all of France

[73] Assignee: P C U K Produits Chimiques Ugine Kuhlmann, Courbevoie, France

[21] Appl. No.: 112,002

[22] Filed: Jan. 14, 1980

[30] Foreign Application Priority Data

Jan. 19, 1979 [FR] France .................................. 79 01326

[51] Int. Cl.$^3$ .............................................. C07C 97/24
[52] U.S. Cl. ........................................................ 260/378
[58] Field of Search ................................. 260/369, 378

[56] References Cited

U.S. PATENT DOCUMENTS

| | | | |
|---|---|---|---|
| 2,276,637 | 3/1942 | Zahn et al. | 260/378 |
| 3,966,775 | 6/1976 | Fukui et al. | 260/378 |

*Primary Examiner*—Winston A. Douglas
*Assistant Examiner*—Raymond K. Covington
*Attorney, Agent, or Firm*—Beveridge, DeGrandi, Kline & Lunsford

[57] ABSTRACT

5-amino-1,2,3,4-tetrahydroanthraquinone, as a new industrial product, is disclosed together with its preparation by reduction from 5-nitro-1,2,3,4-tetrahydroanthraquinone.

10 Claims, No Drawings

5-AMINO-1,2,3,4-TETRAHYDROANTHRAQUINONE AND ITS PREPARATION

The present invention relates to 5-amino-1,2,3,4-tetrahydroanthraquinone as a new industrial product. It also relates to a process for the preparation of this compound by reducing 5-nitro-1,2,3,4-tetrahydroanthraquinone.

The amino derivatives of tetrahydroanthraquinones are useful for the preparation of intermediates in the production of dyestuffs. However, it has not been known up to the present time to prepare 5-amino-1,2,3,4-tetrahydroanthraquinone.

It has now been found, and this is the object of the present invention, that it is possible to obtain 5-amino-1,2,3,4-tetrahydroanthraquinone by reducing 5-nitro-1,2,3,4-tetrahydroanthraquinone. This latter compound is easily prepared by nitrating 1,2,3,4-tetrahydroanthraquinone, 1,2,3,4-tetrahydro-9,10-anthracene diol or 1,2,3,4,4a,9a-hexahydro-9,10-anthracene dione.

The reduction according to the invention is effected either by means of a chemical reducing agent, or by hydrogen in the presence of a catalyst.

When the reduction is effected by means of a chemical reducing agent, the latter compound may advantageously be chosen from among the hydrogenated derivatives of anthraquinone, such as 1,4,4a,9a-tetrahydroanthraquinone, 1,2,3,4,4a,9a-hexahydro-9,10-anthracene dione and 1,2,3,4-tetrahydro-9,10-anthracene diol.

When the reduction is effected by hydrogen, the catalysts which are usually used in hydrogenation are used as catalysts. For example, those based on precious metals such as palladium or platinum and those based on nickel such as Raney nickel may be mentioned.

The reduction is effected in the liquid phase, the 5-nitro-1,2,3,4-tetrahydroanthraquinone being in solution in one of the solvents currently used for hydrogenation reactions. Examples of such solvents include aliphatic, cycloaliphatic or aromatic hydrocarbons; ethers, tetrahydrofuran, dioxane and alcohols. Generally speaking, any solvent which does not comprise a functional hydrogenable group under the reaction conditions may be used.

The reduction may be effected in a wide temperature range varying from 20° C. to 200° C. It is preferable to work between 60° C. and 130° C. In the case of a catalytic hydrogenation, this is effected at atmospheric pressure or under pressure, e.g., of from 2 to 50 bars. The hydrogenation is continued until the theoretical quantity of hydrogen has been absorbed or until there is no longer any absorption of hydrogen.

The following examples illustrate the present invention without limiting it.

EXAMPLE 1

Introduced into a 300 ml autoclave are 200 ml of toluene, 2 g of 5-nitro-1,2,3,4-tetrahydroanthraquinone and 0.02 g of a catalyst based on palladium deposited on carbon containing 5% of palladium. The mixture is heated to 100° C. and hydrogen is introduced under a pressure of 10 bars. An absorption of hydrogen is observed which stops after 2 hours 30 minutes of heating at 100° C. The catalyst is separated by filtration. By concentrating the filtrate to dryness, 1.65 g of a dark red solid are obtained which is constituted by pure 5-amino-1,2,3,4-tetrahydroanthraquinone:

Melting point: 190°-192° C.
Mass: 227.
IR spectrum: $\nu CO$ at 1600 cm$^{-1}$. $\nu NH_2$ at 3350 and 3420 cm$^{-1}$.
NMR Spectrum (DMSO) = 3 aromatic H at $\delta$: 6.9 to 7.6 ppm; 4 methylene H in position 1 and 4 $\delta$: 2.35 ppm; 4 methylene H in position 2 and 3 $\delta$: 1.56 ppm; 1 labile H at $\delta$: 7.7 ppm.

EXAMPLE 2

The operation is conducted as in Example 1 but toluene is replaced by ethanol. The hydrogenation takes 4 hours and 1.6 g of 5-amino-1,2,3,4-tetrahydroanthraquinone are obtained. Melting point: 189°-191° C.

EXAMPLE 3

Introduced into the autoclave of Example 1 are 100 ml of ethanol, 25.7 g of 5-nitro-1,2,3,4-tetrahydroanthraquinone and 0.2 g of a catalyst based on palladium deposited on carbon containing 5% of palladium. The mixture is heated to 60° C. and the hydrogen is introduced under a pressure of 30 bars. The absorption of hydrogen stops after 40 minutes of reaction at 60° C. After separation of the catalyst by filtration and concentration of the filtrate, 21.7 g of 5-amino-1,2,3,4-tetrahydroanthraquinone are obtained.

EXAMPLE 4

Introduced into a glass reactor provided with a mechanical stirrer are 45 ml of amyl alcohol, 3 g of 5-nitro-1,2,3,4-tetrahydroanthraquinone and 7.5 g of 1,2,3,4-tetrahydro-9,10-anthracene diol. The mixture is heated under a nitrogen current for 90 minutes at 60° C. After cooling, 7.7 g of a precipitate are obtained by filtration and the analysis thereof shows that it is a mixture of 5-amino-1,2,3,4-tetrahydroanthraquinone and 1,2,3,4-tetrahydroanthraquinone. The filtrate, which according to thin layer chromatography also contains a mixture of these two compounds, is recyclable.

EXAMPLE 5

The operation is carried out as in Example 4, but the amyl alcohol is replaced by the filtrate of Example 4. After cooling, 9.8 g of a mixture of 1,2,3,4-tetrahydroanthraquinone and 5-amino-1,2,3,4-tetrahydroanthraquinone are obtained by filtration.

What is claimed is:

1. 5-amino-1,2,3,4-tetrahydroanthraquinone, as a new industrial product.

2. A process for the preparation of 5-amino-1,2,3,4-tetrahydroanthraquinone which comprises subjecting 5-nitro-1,2,3,4-tetrahydroanthraquinone to a reduction to a liquid phase.

3. A process according to claim 2 in which the liquid phase comprises a solvent which is devoid of any functional hydrogenable group under the reaction conditions.

4. A process according to claim 2 or 3 in which the reduction is effected by means of a chemical reducing agent.

5. A process according to claim 4 in which the chemical reducing agent is 1,2,3,4-tetrahydro-9,10-anthracenediol.

6. A process according to claim 4 in which the chemical reducing agent is 1,4,4a,9a-tetrahydroanthraquinone.

7. A process according to claim 2 or 3 in which the reduction is effected by means of hydrogen in the presence of a hydrogenation catalyst.

8. A process according to claim 7 in which the hydrogenation catalyst is a catalyst selected from nickel, palladium and platinum.

9. A process according to claim 2 or 3 in which the reaction is effected at a temperature between 20° C. and 200° C.

10. A process according to claim 2 or 3 in which the reaction is effected at a temperature between 60° C. and 130° C.

* * * * *